United States Patent [19]

King et al.

[11] Patent Number: 5,654,433

[45] Date of Patent: Aug. 5, 1997

[54] PROCESS FOR PIPERIDINE DERIVATIVES

[75] Inventors: Chi-Hsin Richard King, Cincinnati; Michele A. Kaminski, Reading, both of Ohio

[73] Assignee: Merrell Pharmaceuticals Inc., Cincinnati, Ohio

[21] Appl. No.: 433,299

[22] Filed: May 3, 1995

Related U.S. Application Data

[60] Division of Ser. No. 369,234, Jan. 6, 1995, which is a continuation-in-part of Ser. No. 152,606, Nov. 15, 1993, abandoned, which is a continuation-in-part of Ser. No. 99,773, Jul. 30, 1993, abandoned, which is a continuation of Ser. No. 17,251, Feb. 25, 1993, abandoned, which is a continuation-in-part of Ser. No. 9,370, Jan. 26, 1993, abandoned, which is a continuation of Ser. No. 867,261, Apr. 10, 1993, abandoned.

[51] Int. Cl.$^6$ .................. C07D 211/22; C07D 211/32
[52] U.S. Cl. .................. 546/241; 546/237; 546/239; 546/240
[58] Field of Search .................. 546/237, 239, 546/240, 241

[56] References Cited

U.S. PATENT DOCUMENTS

| | | | |
|---|---|---|---|
| 3,878,217 | 4/1975 | Carr | 546/240 |
| 3,965,257 | 6/1976 | Carr | 546/240 |
| 4,254,129 | 3/1981 | Carr et al. | 546/239 |
| 4,254,130 | 3/1981 | Carr et al. | 546/237 |
| 4,285,957 | 8/1981 | Carr et al. | 546/237 |
| 4,285,958 | 8/1981 | Carr et al. | 546/239 |
| 4,442,300 | 4/1984 | Olsson et al. | 560/66 |
| 4,443,460 | 4/1984 | Rodrigues et al. | 514/317 |
| 4,952,336 | 8/1990 | Brynes et al. | 252/301.16 |
| 5,057,524 | 10/1991 | Walsh | 514/317 |
| 5,068,432 | 11/1991 | Brown | 564/347 |
| 5,294,623 | 3/1994 | Fukumi et al. | 514/317 |

FOREIGN PATENT DOCUMENTS 3844443  7/1990  Germany .

OTHER PUBLICATIONS

Archiv der Pharmazie, 306, 807–813 (1973).
Morrison & Boyd, Organic Chemistry, Allyn and Bacon, Inc. 1973, P, 528.
Jaeu et al., "Synthesis of the enantiomers of reduced haloperidol", CA115 (15);158935m, 1991.
J. Pharm. Biomed. Anal. (JPBADA,0731-7085/91); vol. 9 (10–12); pp. 929–933 (1991).
Tetrahedron, (Incl. Tetrahedron Reports) vol., 34, 1978, Oxford GB pp. 1651–1660. K. Omura, D. Swern.
Journal of Organic Chemistry. vol. 50, No. 25, 13 Dec. 1985, Easton US, pp. 5446–5448 H.C. Brown et al.
Journal of the Chemical Society, Dalton Trans 1982, Lucthworth GB pp. 1091–1097, L.D. Burek, J.F. Healy.
A Guide to the Chemical Basis of Drug Design, Alfred Burger, p. 15 (1984).
Giddings et al., J. Organ. Chem, vol. 53, pp. 1103–1107 (1988).
Rajendran et al., Synthesis (1995) Feb. pp. 153–154.
Buehler et al., "Organic synthesis" Wiley Science (1970) pp. 760–761.
Torii et al., J. Organ. Chem, vol. 51, pp. 155–161 (1986).
Chan et al., J. Chromatography, vol. 571, pp. 291–297 (1991).
Coutant et al., J. Chromatography, vol. 570, pp. 139–148 (1991).
Chen T.M, et al., J, Phar Biomed Anal (JPBADA, 0731-7085/91): vol.
Simpson, P. et al. Synthetic Communications 21(3), 449–458 (1991).
Jaen et. al. "Synthesis of the enantiomers of reduced hloperidol" Pharm. Res. v.8, 1002–5, (1991) *copies in copending cases SN 08/434,134.

*Primary Examiner*—Ceila Chang
*Attorney, Agent, or Firm*—Charlotte L. Barney

[57] ABSTRACT

The present invention is related to a novel process for preparing certain piperidine derivatives which are useful as antihistamines, antiallergy agents and bronchodilators.

3 Claims, No Drawings

PROCESS FOR PIPERIDINE DERIVATIVES

This is a division of application Ser. No. 08/369,234, filed Jan. 6, 1995, which is a continuation-in-part of Ser. No. 08/152,606, filed Nov. 15, 1993, now abandoned; which is a continuation-in-part of Ser. No. 08/099,773, filed Jul. 30, 1993, now abandoned; which is a continuation of Ser. No. 08/017,251, filed Feb. 25, 1993, now abandoned; which is a continuation-in-part of Ser. No. 08/009,370, filed Jan. 26, 1993, now abandoned; which is a continuation of Ser. No. 07/867,261, filed Apr. 10, 1993, now abandoned.

BACKGROUND OF THE INVENTION

The present invention is related to a novel process for preparing certain piperidine derivatives which are useful as antihistamines, antiallergy agents and bronchodilators [U.S. Pat. No. 4,254,129, Mar. 3, 1981, U.S. Pat. No. 4,254,130, Mar. 3, 1981 and U.S. Pat. No. 4,285,958, Apr. 25, 1981].

These piperidine derivatives can be described by the following formulas:

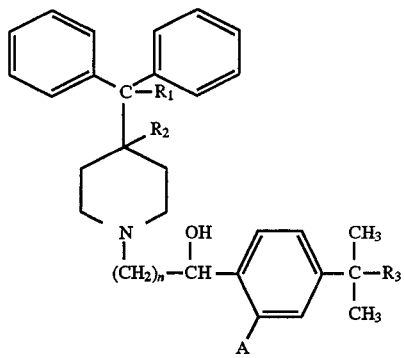

(I)

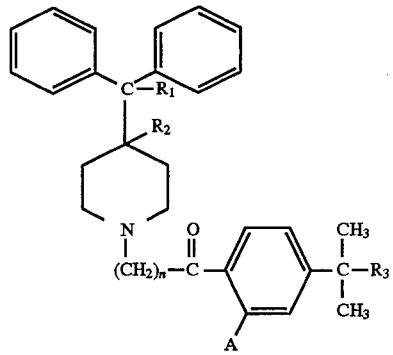

(II)

wherein
  $R_1$ represents hydrogen or hydroxy;
  $R_2$ represents hydrogen; or
  $R_1$ and $R_2$ taken together form a second bond between the carbon atoms bearing $R_1$ and $R_2$;
  n is an integer of from 1 to 5;
  $R_3$ is —$CH_2OH$, —COOH or —COOalkyl wherein the alkyl moiety has from 1 to 6 carbon atoms and is straight or branched;
  each of A is hydrogen or hydroxy; and
  pharmaceutically acceptable salts, hydrates and individual optical isomers thereof.

The novel process for preparing the piperidine derivatives of formula (I) and formula (II) of the present invention offers high yields and ease of purification.

SUMMARY OF THE INVENTION

The present invention provides a novel process for preparing the piperidine derivatives of formula (I) and formula (II)

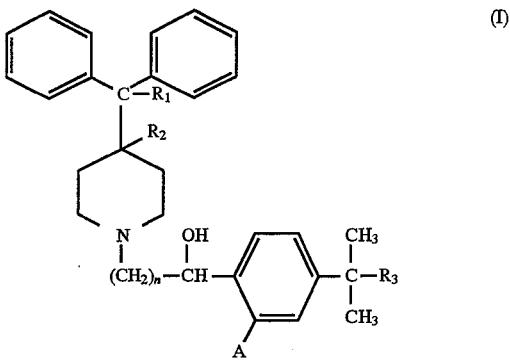

(I)

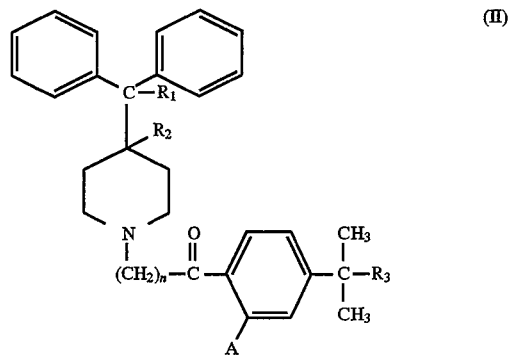

(II)

wherein
  $R_1$ represents hydrogen or hydroxy;
  $R_2$ represents hydrogen; or
  $R_1$ and $R_2$ taken together form a second bond between the carbon atoms bearing $R_1$ and $R_2$;
  n is an integer of from 1 to 5;
  $R_3$ is —$CH_2OH$, —COOH or —COOalkyl wherein the alkyl moiety has from 1 to 6 carbon atoms and is straight or branched;
  each of A is hydrogen or hydroxy; and
  pharmaceutically acceptable salts, hydrates and individual optical isomers thereof comprising the steps of:
  (a) reacting a benzeneacetic acid compound of the formula

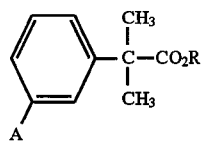

wherein A is as defined above and R is hydrogen or $C_1$–$C_6$ alkyl with a suitable reducing agent to give a phenethyl alcohol;

(b) reacting the phenethyl alcohol with a ω-halo compound of the formula

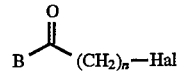

wherein B is halo or hydroxy, Hal represents Cl, Br or I and n is as defined above, in the presence of a suitable Lewis acid to produce a ω-halo hydroxyethylphenylketone; and (c) reacting the ω-halo hydroxyethylphenylketone with a piperidine compound of the formula

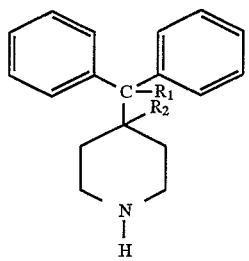

wherein $R_1$ and $R_2$ are as defined above in the presence of a suitable non-nucleophilic base to produce a piperidine hydroxyethylphenylketone derivative of formula (II) wherein $R_3$ is —$CH_2OH$;

(d) optionally reacting the piperidine hydroxyethylphenylketone derivative of formula (II) wherein $R_3$ is —$CH_2OH$ with a suitable oxidizing agent to produce a piperidine carboxyphenylketone derivative of formula (II) wherein $R_3$ is —COOH;

(e) optionally reacting the piperidine carboxyphenylketone derivative of formula (II) wherein $R_3$ is —COOH to produce a piperidine carboxyphenylketone ester derivative of formula (II) wherein $R_3$ is —COOalkyl.

(f) optionally reacting the piperidine carboxyphenylketone derivative of formula (II) wherein $R_3$ is —COOH or the piperidine carboxyphenylketone ester derivative of formula (II) wherein $R_3$ is —COOalkyl with a suitable reducing agent to produce a piperidine carboxyphenylalcohol derivative of formula (I) wherein $R_3$ is —COOH or the piperidine carboxyphenylalcohol ester of formula (I) wherein $R_3$ is —COOalkyl;

(g) optionally reacting the piperidine carboxyphenylalcohol derivative of formula (I) wherein $R_3$ is —COOH to produce a piperidine carboxyphenylalcohol ester derivative of formula (I) wherein $R_3$ is —COOalkyl; and (h) optionally reacting the piperidine hydroxyethylphenylketone derivative of formula (II) wherein $R_3$ is —$CH_2OH$, the piperidine carboxyphenylketone derivative of formula (II) wherein $R_3$ is —COOH, the piperidine carboxyphenylketone ester derivative of formula (II) wherein $R_3$ is —COOalkyl, the piperidine carboxyphenylalcohol derivative of formula (I) wherein $R_3$ is —COOH or the piperidine carboxyphenylalcohol ester of formula (I) wherein $R_3$ is —COOalkyl with an appropriate deprotecting reagent, with the proviso that each of the hydroxy groups present in the compounds described in steps a–g are optionally protected or unprotected.

Alternatively, the present invention provides a novel process for preparing the piperidine derivatives of formula (I) comprising the steps of:

(a) reacting the ω-halo hydroxyethylphenylketone with a suitable reducing agent to produce a ω-halo hydroxyethylphenylalcohol;

(b) reacting the ω-halo hydroxyethylphenylalcohol with a piperidine compound of the formula

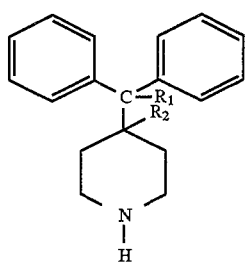

wherein $R_1$ and $R_2$ are as defined above, in the presence of a suitable non-nucleophilic base to produce a piperidine hydroxyethylphenylalcohol derivative of formula (I) wherein $R_3$ is —$CH_2OH$;

(c) optionally reacting the piperidine hydroxyethylphenylalcohol derivative of formula (I) wherein $R_3$ is —$CH_2OH$ with a suitable oxidizing agent to produce a piperidine carboxyphenylalcohol derivative of formula (I) wherein $R_3$ is —COOH; and (d) optionally reacting the piperidine carboxyphenylalcohol derivative of formula (I) wherein $R_3$ is —COOH to produce the piperidine carboxyphenylalcohol ester derivative of formula (I) wherein $R_3$ is —COOalkyl.

(e) optionally reacting the piperidine hydroxyethylphenylalcohol derivative of formula (I) wherein $R_3$ is —$CH_2OH$, the piperidine carboxyphenylalcohol derivative of formula (I) wherein $R_3$ is —COOH or the piperidine carboxyphenylalcohol ester derivative of formula (I) wherein $R_3$ is —COOalkyl with an appropriate deprotecting reagent, with the proviso that each of the hydroxy groups present in the compounds described in steps a–d are optionally protected or unprotected.

In addition, the present invention provides a novel process for preparing the piperidine derivatives of formula (I) comprising the steps of:

(a) reacting the piperidine hydroxyethylphenylketone derivative of formula (II) wherein $R_3$ is —$CH_2OH$ with a suitable reducing agent to produce a piperidine hydroxyethylphenylalcohol derivative of formula (I) wherein $R_3$ is —$CH_2OH$;

(b) optionally reacting the piperidine hydroxyethylphenylalcohol derivative of formula (I) wherein $R_3$ is —$CH_2OH$ with a suitable oxidizing agent to produce a piperidine carboxyphenylalcohol derivative of formula (I) wherein $R_3$ is —COOH; and (c) optionally reacting the piperidine carboxyphenylalcohol derivative of formula (I) wherein $R_3$ is —COOH to produce the piperidine carboxyphenylalcohol ester derivative of formula (I) wherein $R_3$ is —COOalkyl.

(d) optionally reacting the piperidine hydroxyethylphenylketone derivative of formula (II) wherein $R_3$ is —$CH_2OH$, the piperidine hydroxyethylphenylalcohol derivative of formula (I) wherein $R_3$ is —$CH_2OH$, the piperidine carboxyphenylalcohol derivative of formula (I) wherein $R_3$ is —COOH or the piperidine carboxyphenylalcohol ester derivative of formula (I) wherein $R_3$ is —COOalkyl with an appropriate deprotecting reagent, with the proviso that each of the hydroxy groups present in the compounds described in steps a–c are optionally protected or unprotected.

As used herein, straight or branched alkyl groups having from 1 to 6 carbon atoms as referred to herein are methyl, ethyl, n-propyl, isopropyl, n-butyl, sec-butyl, tert-butyl, n-pentyl, neopentyl and n-hexyl.

The piperidine derivatives of the formula (I) and formula (II) can form pharmaceutically acceptable salts. Pharmaceutically acceptable acid addition salts of the compounds of this invention are those of any suitable inorganic or organic acid. Suitable inorganic acids are, for example, hydrochloric, hydrobromic, sulfuric, and phosphoric acids. Suitable organic acids include carboxylic acids, such as, acetic, propionic, glycolic, lactic, pyruvic, malonic, succinic, fumaric, malic, tartaric, citric, cyclamic, ascorbic, maleic, hydroxymaleic, and dihydroxymaleic, benzoic, phenylacetic, 4-aminobenzoic, 4-hydroxybenzoic, anthranillic, cinnamic, salicyclic, 4-aminosalicyclic, 2-phenoxybenzoic, 2-acetoxybenzoic, and mandelic acid, sulfonic acids, such as, methanesulfonic, ethanesulfonic and β-hydroxyethanesulfonic acid. Non-toxic salts of the compounds of the above-identified formula formed with inorganic or organic bases are also included within the scope of this invention and include, for example, those of alkali metals, such as, sodium, potassium and lithium, alkaline earth metals, for example, calcium and magnesium, light metals of group IIIA, for example, aluminum, organic amines, such as, primary, secondary or tertiary amines, for example, cyclohexylamine, ethylamine, pyridine, methylaminoethanol and piperazine. The salts are prepared by conventional means as, for example, by treating a piperidine derivative of formula (I) or formula (II) with an appropriate acid or base.

As used herein, the term "hydrate" refers to a combination of water with a compound of formula (I) or (II) wherein the water retains its molecular state as water and is either absorbed, adsorbed or contained within a crystal latice of the substrate molecule of formula (I) or (II).

As used herein, the term "adsorped" refers to the physical state wherein the water molecule in the hydrated, pharmaceutically acceptable acid addition salts of piperidine derivatives of the formula (I) and (II) is distributed over the surface of the solid hydrated, pharmaceutically acceptable acid addition salts of piperidine derivatives of the formula (I) and (II).

As used herein, the term "absorbed" refers to the physical state wherein the water molecule in the hydrated, pharmaceutically acceptable acid addition salts of piperidine derivatives of the formula (I) and (II) is distribued throughout the body of the solid hydrated, pharmaceutically acceptable acid addition salts of piperidine derivatives of the formula (I) and (II).

Hydrated, pharmaceutically acceptable acid addition salts of the compounds of formula (I) and (II) are those hydrates ranging from essentially 0.10 to 5 molecules of water per molecule of substrate salt of formula (I) or (II).

The novel process for preparing the piperidine derivatives of formula (I) and formula (II) is outlined in Scheme A. In Scheme A, all substituents are as previously defined unless otherwise indicated.

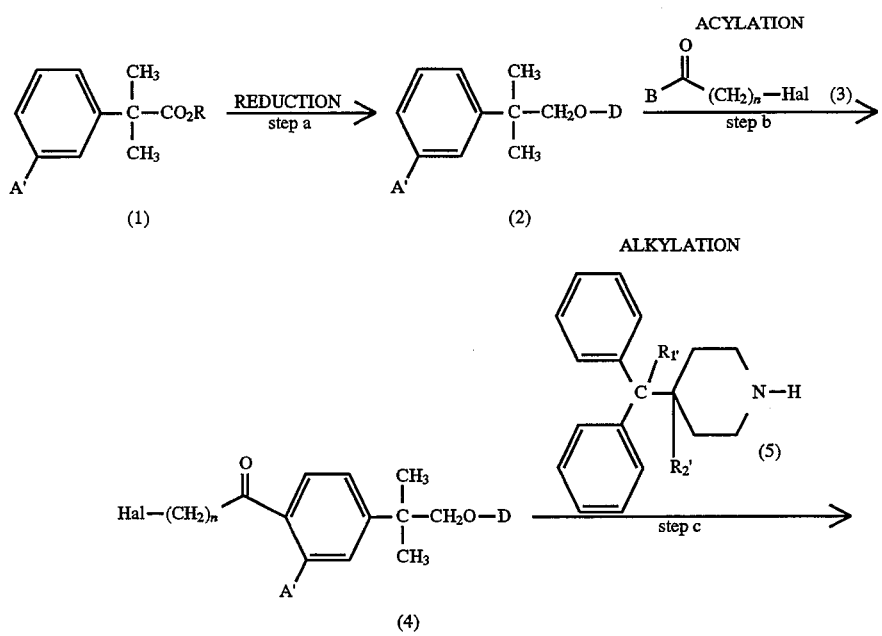

-continued
Scheme A

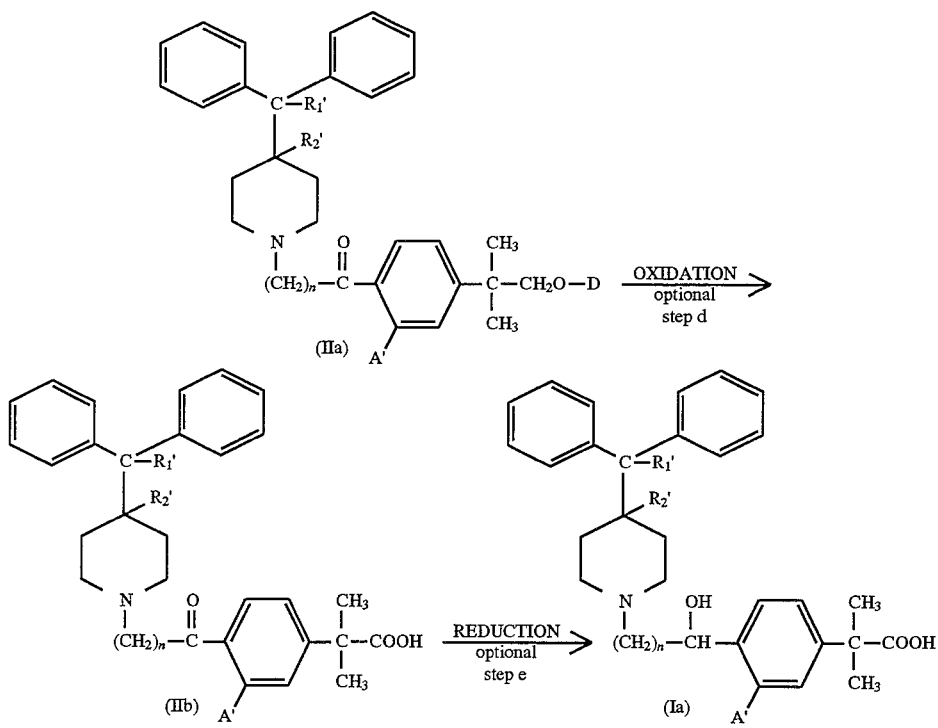

A'=hydrogen, protected hydroxy or hydroxy
B=Halo or OH
D=hydrogen or a suitable protecting group
$R_1'$ and $R_2'$=hydrogen, protected hydroxy, hydroxy or taken togther to form a second bond between the carbon atoms bearing $R_1'$ and $R_2'$
R=$C_1$–$C_6$ alkyl or hydrogen Scheme A provides a general synthetic procedure for preparing the piperidine derivatives of formula (I) and formula (II).

In step a, the carboxy functionality of an appropriate benzeneacetic acid compound of structure (1), wherein R is hydrogen or $C_1$–$C_6$ alkyl, is reduced to give the corresponding phenethyl alcohol of structure (2), wherein D is hydrogen.

For example, reduction of the appropriate benzeneacetic acid of structure (1), wherein R is hydrogen, using, for example, sodium bis(2-methoxyethoxy)aluminum hydride, lithium aluminum hydride, diborane or aluminum hydride with diborane being preferred. Reduction of the appropriate benzeneactic acid of structure (1), wherein R is $C_1$–$C_6$ alkyl, using, for example, lithium aluminum hydride, lithium borohydride, sodium bis(2-methoxyethoxy)aluminum hydride, aluminum hydride, lithium triethylborohydride and lithium tri-sec-butylborohydride with lithium aluminum hydride being preferred. Suitable solvents are ethers, for example, diethyl ether, tetrahydrofuran or dioxane. These reduction reactions are carried out at temperatures ranging from about 0° C. to the reflux temperature of the solvent, and the reaction time varies from about ½ hour to 8 hours.

The starting benzeneacetic acid compounds of structure (1) are known in the art of are prepared by procedures well known in the art. For example, the benzeneacetic acid compound of structure (1) wherein R is $C_1$–$C_6$ alkyl and A' is hydroxy may be prepared by treating a hot solution of 1 equivalent of an appropriate straight or branched alkyl $C_{1-6}$ ester of 3-trifluoroacetoxyphenylacetic acid in dimethoxyethane with a base, such as, sodium hydride under a nitrogen atmosphere followed by the addition of 2.1 equivalents of methyliodide in dimethoxyethane to the mixture over about a 20 minute period. The mixture is refluxed for about 3 hours then concentrated to remove most of the solvent after which diethyl ether, then water are added cautiously. The organic layer is separated, extracted with ether, dried over magnesium sulfate and distilled to give the appropriate ester of the benzeneacetic acid compound of structure (1) wherein A' is a trifluoroacetoxy protected hydroxy and R is $C_1$–$C_6$ alkyl. To a solution of the methylated ester in 50% alcohol/water is added 3X molar amount of potassium carbonate. The solution is stirred at about 25° C. for about 8 hours then concentrated to a semisolid at reduced pressure at about 50° C. and upon cooling water is added and the mixture is neutralized with dilute hydrochloric acid then extracted with ether. The ether extract is dried over magnesium sulfate, filtered and concentrated to give the appropriate ester of the benzeneacetic acid compound of structure (1) wherein A' is hydroxy and R is $C_1$–$C_6$ alkyl. The esters of the benzeneacetic acid compounds of structure (1) wherein A' is a trifluoroacetoxy protected hydroxy and R is $C_1$–$C_6$ alkyl are known in the art, for example, from ethyl m-hydroxyphenylacetate by treatment with trifluoroacetic anhydride.

Alternatively, the phenethyl alcohol compounds of structure (2) may be prepared by Friedel-Crafts acylation of an appropriate benzene compound with a suitable protected 2-methyl-2-propenyl alcohol compound. For example, the phenethyl alcohol compound of structure (2) wherein A' is hydrogen, hydroxy or a suitably protected hydroxy may be prepared by reacting an appropriate 2-methyl-2-propenyl alcohol compound with an appropriate benzene compound in the presence of $AlCl_3$.

In step b, the appropriate phenethyl alcohol of structure (2), wherein A' is hydrogen, hydroxy or a suitably protected hydroxy, is acylated with the ω-halo compound of structure (3) wherein B is halo under Freidel-Crafts conditions to give the corresponding ω-halo hydroxyethylphenylketone of structure (4) wherein A' is described as above.

For example, the ω-halo hydroxyethylphenylketone of structure (4), wherein A' is hydrogen, hydroxy or a protected hydroxy, may be prepared by reacting an appropriate phenyethyl alcohol of structure (2), wherein A' is hydrogen, hydroxy or a protected hydroxy, with a appropriate ω-halo compound of structure (3) wherein B is halo, which are known in the art or are prepared by procedures well known in the art, under the general conditions of a Friedel-Crafts acylation using a suitable Lewis acid. The reaction is carried out in a solvent, such as carbon disulfide, methylene chloride, tetrachloroethane or nitrobenzene with methylene chloride being the preferred solvent. The reaction time varies from about ½ hour to 8 hours, preferably 1 to 5 hours and the reaction temperature varies from about 0° C. to 25° C. The ω-halo hydroxyethylphenylketone of structure (4) wherein A' is hydrogen, hydroxy or a protected hydroxy is recovered from the reaction zone by an aqueous quench followed by extraction as is known in the art. The ω-halo hydroxyethylphenylketone of structure (4) wherein A' is hydrogen, hydroxy or a protected hydroxy may be purified by procedures well known in the art, such as crystallization.

Alternatively, the appropriate phenethyl alcohol of structure (2) wherein A' is hydroxy may be acylated with the ω-halo compound of structure (3) wherein B is hydroxy in the presence of a Lewis acid to give the corresponding halo hydroxyethylphenylketone of structure (4) as described in *Arch. Pharm.* 306, 807 1973. In general, an appropriate phenethyl alcohol of structure (2), wherein A' is hydroxy, and the ω-halo compound of structure (3), wherein B is hydroxy, are melted together at about 50° C., then cooled to about 10° C. after which a Lewis acid is added in an amount about 2.2 times the molar amount of the appropriate phenethyl alcohol of structure (2), wherein A' is hydroxy, employed. The mixture is heated at about 70° C. for about 2 hours after which a 30% sodium acetate solution is added and extracted with ether. The organic layer is dried and the solvent evaporated to give the ω-halo hydroxyethylphenylketone of structure (4) wherein A' is hydroxy. The ω-halo hydroxyethylphenylketone of structure (4) may be purified by procedures well known in the art, such as crystallization.

Suitable Lewis acids for the acylation reaction described in step b are well known and appreciated in the art. Examples of suitable Lewis acids are boron trichloride, aluminum chloride, titanium tetrachloride, boron trifluoride, tin tetrachloride and zinc chloride. The selection and utilization of suitable Lewis acids for the acylation reaction of step b is well known and appreciated by one of ordinary skill in the art.

The starting ω-halo compounds of (3) are commercially available of easily prepared by generally known methods.

While not necessary for utilization in the acylation reaction of step b, the hydroxyethyl functionality of those phenethyl alcohols of structure (2) may be protected with a suitable protecting group. The selection and utilization of suitable protecting groups for the phenethyl alcohols of structure (2) is well known by one of ordinary skill in the art and is described in "Protective Groups in Organic Syntheses", Theodora W. Greene, Wiley (1981). For example, suitable protecting groups for the hydroxyethyl functionality include ethers such as tetrahydrothiopyranyl, tetrahydrothiofuranyl, 2-(phenylselenyl)ethyl ether, o-nitrobenzyl ether, trimethylsilyl ether, isopropyldimethylsilyl ether, t-butyldimethytsilyl ether, t-butyldiphenylsilyl ether, tribenzylsilyl ether, triisopropylsilyl ether; and esters, such as acetate ester, isobutyrate ester, pivaloate ester, adamantoate ester, benzoate ester, 2,4,6-trimethylbenzoate (mesitoate) ester, methyl carbonate, p-nitrophenyl carbonate, p-nitrobenzyl carbonate, S-benzyl thiocarbonate and N-phenylcarbamate, with acetoxy being preferred.

For those ω-halo hydroxyethylphenylketone of structure (4), wherein A' is hydrogen, hydroxy or a protected hydroxy and D is hydrogen, the Friedel-Crafts acylation may result in acylation of the hydroxyethyl functionality and will require deprotection prior to the oxidation reaction described in optional step d. Suitable deprotecting agents and methods are described in optional step d, infra.

While also not necessary for utilization in the acylation reaction of step b, the phenol functionality of those phenethyl alcohols of structure (2), wherein A' is hydroxy may be protected with a suitable protecting group. For example, suitable protecting groups for the phenolic hydroxy include methyl ether, 2-methoxyethoxymethyl ether (MEM), cyclohexyl ether, o-nitrobenzyl ether, 9-anthryl ether, t-butyldimethylsilyl ether, acetate, benzoate, methyl carbamate, benzyl carbamate, aryl pivaloate and aryl methanesulfonate.

In step c, the ω-halo functionality of the appropriate ω-halo hydroxyethylphenylketone of structure (4) is alkylated with the appropriate piperidine compound of structure (5) to give the corresponding piperidine hydroxyethylphenylketone derivative of formula (II) wherein $R_3$ is —$CH_2OH$.

For example, the alkylation reaction is carried out in a suitable solvent preferably in the present of a base and optionally in the presence of a catalytic amount of an iodide source, such as potassium or sodium iodide, for about 4 to 120 hours and at temperatures of about 70° C. to the reflux temperature of the solvent. Suitable solvent for the alkylation reaction include alcohol solvents such as, methanol, ethanol, isopropyl alcohol, or n-butanol; ketone solvents, such as, methyl isobutyl ketone; hydrocarbon solvents, such as, benzene, toluene or xylene; halogenated hydrocarbons, such as, chlorobenzene or methylene chloride or dimethylformamide. Suitable bases for the alkylation reaction include inorganic bases, for example, sodium bicarbonate, potassium carbonate, or potassium bicarbonate or organic bases, such as, a trialkylamine, for example, triethylamine or pyridine, or an excess of an appropriate piperidine compound of structure (5) may be used.

For those piperidine compounds of structure (5), wherein $R_1$ is hydroxy, it is preferred that $R_1$ be unprotected for utilization in the alkyation reaction of step c, but those hydroxy functionalities present in the piperidine compounds of structure (5), wherein $R_1$ is hydroxy may be protected with a suitable protecting group. The selection and utilization of suitable protecting groups for the piperidine compounds of structure (5), wherein $R_1$ is hydroxy is well known by one of ordinary skill in the art and is described in "Protective Groups in Organic Syntheses", Theodora W. Greene, Wiley (1981). For example, suitable protecting groups for those hydroxy functionalities present include ethers such as tetrahydrothiopyranyl, tetrahydrothiofuranyl, 2-(phenylselenyl)ethyl ether, o-nitrobenzyl ether, trimethylsilyl ether, isopropyldimethylsilyl ether, t-butyldimethylsilyl ether, t-butyldiphenylsilyl ether, tribenzylsilyl ether, triisopropylsilyl ether; and esters, such as acetate ester, isobutyrate ester, pivaloate ester, adamantoate ester, benzoate ester, 2,4,6-trimethylbenzoate (mesitoate) ester, methyl carbonate, p-nitrophenyl carbonate, p-nitrobenzyl carbonate, S-benzyl thiocarbonate and N-phenylcarbamate.

The piperidine compounds of structure (5) wherein $R_1$ and $R_2$ are hydrogen and where $R_1$ is hydroxy and $R_2$ is hydrogen are readily available to one or ordinary skill in the art. The piperidine compounds of structure (5) wherein $R_1$ and $R_2$ form a second bond between the carbon atoms bearing $R_1$ and $R_2$ may be prepared by dehydration of the corresponding compound wherein $R_1$ is hydroxy by procedures generally known in the art.

In optional step d, the hydroxyethyl functionality of the appropriate piperidine hydroxyethylphenylketone derivative of formula (II) wherein $R_3$ is —$CH_2OH$ is oxidized to give the corresponding piperidine carboxyphenylketone derivative of formula (II) wherein $R_3$ is COOH.

For example, oxidation of the appropriate piperidine hydroxyethylphenylketone derivative of formula (II) wherein $R_3$ is —$CH_2OH$ may be achieved using a variety of oxidizing agents and methods.

One such method involves a two-step procedure in which the hydroxyethyl functionality of the appropriate piperidine hydroxyethylphenylketone derivative of formula (II) wherein $R_3$ is —$CH_2OH$ is first oxidized to the corresponding aldehyde functionality using, for example, Swern Oxidation conditions (dimethyl sulfoxide, oxyalyl chloride and triethylamine), as is known in the art. The Swern Oxidation is carried out in suitable aprotic organic solvents such as methylene chloride at temperatures ranging from about –78° C. to room temperature, and the reaction time varies from about ½ hour to 8 hours. Other suitable reagents for the oxidation of the hydroxyethyl functionality of the appropriate piperidine hydroxyethylphenylketone derivative of formula (II) wherein $R_3$ is —$CH_2OH$ to the corresponding aldehyde functionality are Dess-Martin reagent, chromium (IV) oxide, nickel peroxide, sodium dichromate, potassium dichromate, t-butyl chromate, silver oxide, argentic picolinate manganese dioxide lead tetraacetate, dicyclohexylcarbodiimide, 2,3-dichloro-5,6-dicyanoquinone, tetrachloro-1,2-benzoquinone, 2,2,6,6-tetramethylpiperidinyl-1-oxy (TEMPO) or quinolinium chlorochromate.

Aternatively, an intermediate aldehyde compound may be prepared by administering terfenadine to human subjects, collecting the urine, basifying with a suitable base, such as sodium hydroxide and extracting into an organic solvent, such as ethyl acetate. After evaporation of the organic solvent and dissolving the residue in a suitable solvent such as methanol/water, the intermediate aldehyde compound may be purified by HPLC using, for example, a Spherisorb 5 micrometer CN, 25 cm×4.6 mm ID column; acetonitrile/0.05M ammonium acetate, pH 4.5 (40/60, v/v) mobile phase; and 1.2 mL/min flow rate.

The intermediate aldehyde compound is then oxidized further to give the corresponding piperidine carboxyphenylketone derivative of formula (II) wherein $R_3$ is —COOH using, for example, potassium permanganate. The potassium permanganate oxidation is carried out in a suitable acidic medium such as hydrochloric acid/acetone at a temperature ranging from about 0° C. to room temperature and the reaction time varies from about ½ hour to 8 hours. Other suitable reagents for the oxidation of the intermediate aldehyde to the corresponding piperidine carboxyphenylketone derivative of formula (II) wherein $R_3$ is —COOH are chromium (IV) oxide, silver (I) oxide, silver oxide, argentic picolinate, peroxide, nitric acid, m-chloroperbenzoic acid and peracetic acid.

Another method involves a one-step procedure in which the hydroxyethyl functionality of the appropriate piperidine hydroxyethylphenylketone derivative of formula (II) wherein $R_3$ is —$CH_2OH$ is oxidized directly to the carboxy functionality to give the corresponding piperidine carboxyphenylketone derivative of formula (II) wherein $R_3$ is —COOH. Oxidizing reagents suitable for direct, one-step oxidation of the hydroxyethyl functionality to the carboxy functionality include, for example, chromaium (IV) oxide, potassium permanganate, nitric acid, nitrogen dioxide, ruthenium (VIII) oxide, nickel peroxide, silver oxide, t-butyl chromate and xenic acid.

Oxidation using Swern Oxidation conditions, nickel peroxide, chromium (IV) oxide, silver oxide, sodium dichromate, potassium dichromate, manganese dioxide, 2,3-dichloro-5,6-dicyanoquinone and tetrachloro-1,2-benzoquinone is preferred for those piperidine hydroxyethylphenylketone derivatives of formula (II) wherein $R_3$ is —$CH_2OH$ wherein $R_1$ and $R_2$ taken together form a second bond between the carbon atoms bearing $R_1$ and $R_2$.

As one skilled in the art would appreciate, those piperidine hydroxyethylphenylketone derivatives of formula (II) wherein $R_3$ is —$CH_2OH$ wherein the hydroxyethyl functionality is protected must be reacted with an appropriate deprotecting reagent prior to the oxidation reaction described in step d. The selection and utilization Of appropriate deprotecting reagents is well known by one of ordinary skill in the art and is described in "Protective Groups in Organic Syntheses", Theodora W. Greene, Wiley (1981). Examples of appropriate deprotecting reagents are mineral acids, strong organic acids, Lewis acids, aqueous mineral bases, catalytic hydrogenation and the like. For example, cleavage of an acetate ester protecting group on the hydroxyethyl functionality of the piperidine hydroxyethylphenylketone derivatives of formula (II) wherein $R_3$ is —$CH_2OH$ can be achieved by using a base, such as sodium methoxide in methanol as is known in the art. Other methods known in the art for acetate ester cleavage include potassium carbonate in methanol, methanolic ammonia, sodium hydroxide/pyridine in methanol and potassium cyanide in ethanol.

In optional step e, the ketone functionality of the appropriate piperidine carboxyphenylketone derivatives of formula (II) wherein $R_3$ is —$CH_2OD$ or —COOH is reduced to give the corresponding piperidine carboxyphenylalcohol derivatives of formula (I) wherein $R_3$ is —$CH_2OD$ or —COOH.

For example, reduction of the appropriate piperidine carboxyphenylketone derivatives of formula (II) wherein $R_3$ is —$CH_2OD$ or —COOH, using, for example, sodium borohydride, potassium borohydride, sodium cyanoborohydride, or tetramethylammonium borohydride is carried out in lower alcohol solvents, such as, methanol, ethanol, isopropyl alcohol or n-butanol at temperatures ranging from about 0° C. to the reflux temperature of the solvent, and the reaction time varies from about ½ hour to 8 hours. Other suitable reducing agents are, for example, lithium tri-tert-butylaluminohydride and diisobutylaluminum hydride. These reduction reactions are carried out in suitable solvents diethyl ether, tetrahydrofuran or dioxane at temperatures ranging from about 0° C. to the reflux temperature of the solvent, and the reaction time varies from about ½ hour to 8 hours.

Catalytic reduction may also be employed in the preparation of appropriate piperidine carboxyphenylalcohol derivatives of formula (I) wherein $R_3$ is —$CH_2OD$ or —COOH from an appropriate piperidine carboxyphenylketone derivatives of formula (II) wherein $R_3$ is —$CH_2OD$ or —COOH, using, for example, Raney nickel, palladium, platinum or rhodium catalysts in lower alcohol solvents, such as, methanol, ethanol, isopropyl alcohol or n-butanol or acetic acid or their aqueous mixtures, or by the use of aluminum isopropoxide in isopropyl alcohol.

Reduction using sodium borohydride or potassium borohydride is preferred over catalytic reduction for those piperidine carboxyphenylketone derivatives of formula (II) wherein $R_3$ is —$CH_2OD$ or —COOH wherein $R_1$ and $R_2$ taken together form a second bond between the carbon atoms bearing $R_1$ and $R_2$.

In addition, a chiral reduction of the appropriate piperidine carboxyphenylketone derivatives of formula (II) wherein $R_3$ is —$CH_2OD$ or —COOH, using, for example, (+)-B-chlorodiisopinocamphenylborane gives the corresponding (R)-piperidine carboxyphenylalcohol derivatives of formula (I) wherein $R_3$ is —$CH_2OD$ or —COOH and (−)-B-chlorodiisopinocamphenylborane gives the corresponding (S)-piperidine carboxyphenylalcohol derivatives of formula (I) wherein $R_3$ is —$CH_2OD$ or —COOH. Other suitable chiral reducing agents are, (R) and (S)-oxazaborolidine/$BH_3$, potassium 9-O-(1,2:5,6-di-O-isopropylidene-α-D-glucofuransoyl)-9-boratabicyclo[3.3.1]nonane, (R) and (S)-B-3-pinanyl-9-borabicyclo[3.3.1]nonane, NB-Enantride, Lithium (R)-(+) and (S)-(−)-2,2'-dihydroxy-1,1'-binaphthyl alkoxyl aluminum hydride, (R)-(+) and (S)-(−)-2,2'-dihydroxy-6,6'-dimethylbiphenyl borane-amine complex, tris[[(1S,2S,5R)-2-isopropyl-5-methyl-cyclohex-1-yl]methyl]aluminum, [[(1R,3R)-2,2-dimethylbicyclo[2.2.1]hept-3-yl]methyl]beryllium chloride, (R)-BINAP-ruthenium complex/$H_2$ and 6,6'-bis (diphenylphosphino)-3,3'-dimethoxy-2,2',4,4'-tetramethyl-1,1'-biphenyl.

As one skilled in the art would appreciate, the carboxy functionalities of the piperidine carboxyphenylketone derivatives of formula (II) wherein $R_3$ is —COOH and piperidine carboxyphenylalcohol derivatives of formula (I) wherein $R_3$ is —COOH may be esterified by techniques and procedures well known and appreciated by one of ordinary skill in the art to give the corresponding piperidine carboxyphenylketone ester derivatives of formula (II) wherein $R_3$ is —COOalkyl and piperidine carboxyphenylalcohol ester derivatives of formula (I) wherein $R_3$ is —COOalkyl.

For example, one such method involves reacting an appropriate piperidine carboxyphenylketone derivative of formula (II) wherein $R_3$ is —COOH with an excess of an appropriate HOalkyl wherein the alkyl moiety has from 1 to 6 carbon atoms and is straight or branched in the presence of a small amount of mineral acid, e.g. sulfuric acid at reflux. Another suitable method involves reacting an appropriate piperidine carboxyphenylketone derivative of formula (II) wherein $R_3$ is —COOH or piperidine carboxyphenylalcohol derivative of formula (I) wherein $R_3$ is —COOH with an excess of diazomethane in a suitable solvent such as ether at room temperature to give the methyl ester. In addition, the piperidine carboxyphenylketone ester derivatives of formula (II) wherein $R_3$ is —COOalkyl or piperidine carboxyphenylalcohol ester derivatives of formula (I) wherein $R_3$ is —COOalkyl may also be prepared by reacting an appropriate piperidine carboxyphenylketone derivatives of formula (II) wherein $R_3$ is —COOH or piperidine carboxyphenylalcohol derivatives of formula (I) wherein $R_3$ is —COOH with an excess of 2,2-dimethoxypropane in a suitable solvent such as methanol at 0° C. to room temperature to give the methyl ester. Another suitable method involves first reacting an appropriate piperidine carboxyphenylketone derivatives of formula (II) wherein $R_3$ is —COOH with thionyl chloride in a suitable solvent such as methylene chloride to give an intermediate acid chloride, followed by addition of a suitable alcohol of the formula HOalkyl wherein the alkyl moiety has from 1 to 6 carbon atoms and is straight or branched.

As one skilled in the art would appreciate, the reduction of the ketone functionality of the appropriate piperidine carboxyphenylketone derivatives of formula (II) wherein $R_3$ is —COOH described in optional step e can be conducted on the ω-halo hydroxyethylphenylketone of structure (4) or piperidine hydroxyethylphenylketone derivatives of formula (II) wherein $R_3$ is —$CH_2OH$.

For example, reduction of an appropriate ω-halo hydroxyethylphenylketone of structure (4) using the techniques and methods described previously in step e gives the corresponding ω-halo hydroxyethylphenylalcohol. The resulting benzylic alcohol functionality may be optionally protected using the protecting groups described previously for hydroxyethyl in step b. The ω-halo hydroxyethylphenylalcohol so formed is then subjected to the alkylation reaction with an appropriate piperidine compound of structure (5) described previously in step c to give the corresponding piperidine hydroxyethylphenylalcohol derivative of formula (I) wherein $R_3$ is protected or unprotected —$CH_2OH$. The appropriate piperidine hydroxyethylphenylalcohol derivative of formula (I) wherein $R_3$ is —$CH_2OH$ is then subjected to the oxidation reaction described previously in step d using a selective oxidizing agent such as 2,2,6,6-tetramethylpiperidinyl-1-oxy (TEMPO) or quinolinium chlorochromate to give the intermediate aldehyde followed by oxidation with silver oxide to give the corresponding piperidine carboxyphenylalcohol derivative of formula (I) wherein $R_3$ is —COOH. Reduction of an appropriate piperidine hydroxyethylphenylketone derivative of formula (II) wherein $R_3$ is protected or unprotected —$CH_2OH$ using the techniques and methods described previously in step e gives the corresponding piperidine hydroxyethylphenylalcohol derivative of formula (I) wherein $R_3$ is —$CH_2OH$ which is then subjected to the oxidation reaction described previously in step d using a selective oxidizing agent such as 2,2,6,6-tetramethylpiperidinyl-1-oxy (TEMPO) or quinolinium chlorochromate to give the intermediate aldehyde followed by oxidation with silver oxide to give the corresponding piperidine carboxyphenylalcohol derivative of formula (I) wherein $R_3$ is —COOH.

As one skilled in the art would appreciate, the benzeneacetic acid compounds of structure (1), the phenethyl alcohols of structure (2), the ω-halo hydroxyethylphenylketones of structure (4), piperidine compounds of structure (5), piperidine hydroxyethylphenylketone derivatives of formula (II) wherein $R_3$ is —$CH_2OH$, the piperidine carboxyphenylketone derivatives of formula (II) wherein $R_3$ is —COOH, the piperidine carboxyphenylketone ester derivatives of formula (II) wherein $R_3$ is —COOalkyl, the piperidine hydroxyethylphenylalcohol derivatives of formula (I) wherein $R_3$ is —$CH_2OH$, the piperidine carboxyphenylalcohol derivatives of formula (I) wherein $R_3$ is COOH or the piperidine carboxyphenylalcohol ester derivatives of formula (I) wherein $R_3$ is —COOalkyl which bear hydroxy or phenolic functionalities may be protected prior to use in the synthesis depicted in Scheme A using suitable protecting groups as described previously in step b.

As one skilled in the art would appreciate, the benzeneactic acids of structure (1), the phenethyl alcohols of structure (2), the ω-halo hydroxyethylphenylketones of structure (4), piperidine compounds of structure (5), piperidine hydroxyethylphenylketone derivatives of formula (II) wherein $R_3$ is —$CH_2OH$, the piperidine carboxyphenylketone derivatives of formula (II) wherein $R_3$ is —COOH or the piperidine carboxyphenylketone ester derivatives of formula (II) wherein $R_3$ is —COOalkyl, the piperidine hydroxyethylphenylalcohol derivatives of formula (I) wherein $R_3$ is —CH$_2$OH, the piperidine carboxyphenylalcohol derivatives of formula (I) wherein $R_3$ is COOH or the piperidine carboxyphenylalcohol ester derivatives of formula (I) wherein $R_3$ is COOalkyl which bear protected hydroxy or phenolic functionalities may be reacting with prior appropriate deprotecting reagents prior to use in the synthesis depicted in Scheme A. The selection and utilization of appropriate deprotecting reagents is well known by one of ordinary skill in the art and is described in "Protective Groups in Organic Syntheses", Theodora W. Greene, Wiley (1981). Examples of appropriate deprotecting reagents are mineral acids, strong organic acids, Lewis acids, aqueous mineral bases, catalytic hydrogenation and the like.

For example, cleavage of an acetate ester protecting group on the hydroxyethyl functionality of any of the ω-halo hydroxyethylphenylketones of structure (4), piperidine compounds of structure (5), piperidine hydroxyethylphenylketone derivatives of formula (II) wherein $R_3$ is —CH$_2$OH or piperidine hydroxyethylphenylalcohol derivatives of formula (I) wherein $R_3$ is —CH$_2$OH can be achieved by using a base, such as sodium methoxide in methanol as is known in the art. Other methods known in the art for acetate ester cleavage include potassium carbonate in methanol, methanolic ammonia, sodium hydroxide/pyridine in methanol and potassium cyanide in ethanol.

Cleavage of β-methoxyethoxymethyl (MEM) protecting groups on any of those ω-halo hydroxyethylphenylketones of structure (4), piperidine compounds of structure (5), piperidine hydroxyethylphenylketone derivative of formula (II) wherein $R_3$ is —CH$_2$OH, piperidine carboxyphenylketone derivative of formula (II) wherein $R_3$ is —COOH, piperidine carboxyphenylketone ester derivatives of formula (II) wherein $R_3$ is —COOalkyl, piperidine carboxyphenylalcohol derivatives of formula (I) wherein $R_3$ is —COOH, piperidine carboxyphenylalcohol ester derivatives of formula (I) wherein $R_3$ is —COOalkyl or piperidine hydroxyethylphenylalcohol derivatives of formula (I) wherein $R_3$ is —CH$_2$OH wherein A is hydroxy, for example, can be achieved by using trifluoroacetic acid at room temperature or using 5 to 8 equivalents of powdered anhydrous zinc bromide in methylene chloride at about 25° C. by the general procedure of E. J. Corey et al., *Tetrahedron Letters*, 11, 809–812 1976.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C." refers to degrees Celsius; "mm Hg" refers to millimeters of mercury; "μL" refers to microliters; "μg" refers to micrograms; and "μM" refers to micromolar.

EXAMPLE 1

4-[4-[4-(Hydroxydiphenylmethyl)-1-piperidinyl]-1-hydroxybutyl]-α,α-dimethylbenzeneacetic acid hydrochloride

METHOD A

Step a: 2,2-Dimethyl-phenethyl acetate

Dissolve α,α-dimethylphenyl acetic acid (140.0 g, 0.853 mol) in anhydrous tetrahydrofuran (100 mL) and place under a nitrogen atmosphere. Add, by dropwise addition, a solution of lithium aluminum hydride (639 mL of a 1.0M solution in tetrahydrofuran, 24.3 g, 0.639 mol) over a period of approximately 2 hours. Quench with deionized water (24 mL), with 15% aqueous sodium hydroxide (24 mL) and again with deionized water (72 mL). Stir the milky white mixture for 20 minutes, filter through filter aid, dry (MgSO$_4$) and filter through filter aid once more. Evaporate the solvent in vacuo to give 2,2-dimethylphenethyl alcohol as a clear yellow oil.

Dissolve 2,2-dimethylphenethyl alcohol (118.0 g, 0.786 mol) in pyridine (700 mL). Add, by dropwise addition, acetic anhydride (222 mL, 240.7 g, 2.358 mol) and stir overnight at room temperature. Evaporate the solvent in vacuo and purify by distillation to give the title compound as a clear colorless oil; bp 75° C.@0.4 mmHg.

METHOD B

Dissolve 2-methyl-2-propenyl acetate (1.28 mmol) in benzene (80 mL) and add to a stirred solution of AlCl$_3$ (172.3 g, 1.29 mol) in benzene (800 mL) at –10° C. over 45 minutes under a stream of nitrogen. Stir at 5° C. for 20 minutes, pour onto ice (800 g) and stir for 10 minutes. Separate the organic phase, dry (MgSO4) and evaporate the solvent in vacuo (30° C./60 torr). Purify by distillation to give the title compound.

Step b: 4-(4-Chloro-1-oxobutyl)-2,2-dimethylphenethyl acetate

Charge a flask with aluminum chloride (223 g, 1.68 mol) and methylene chloride (200 mL). Place under a nitrogen atmosphere, cool to 0°–5° C. and add, by dropwise addition, ω-chlorobutyryl chloride (188.6 g, 1.34 mol). After acid chloride addition is complete, add, by dropwise addition, 2,2-dimethylphenethyl acetate (128.0 g, 0.67 mol), keeping the temperature at approximately 0° C. Continue stirring at 0° C. for 2 hours, quench by slowly pouring over approximately 2 L of crushed ice. Add methylene chloride (500 mL) and stir for 5 minutes. Separate the organic phase and extract the aqueous phase with methylene chloride (300 mL). Combine the organic phases and wash with saturated aqueous sodium hydrogen carbonate (3×200 mL), with deionized water (200 mL) and brine (200 mL). Dry (MgSO$_4$) and stir for 30 minutes before filtering. Evaporate the solvent in vacuo and purify by chromatography (ethyl acetate/hexane) to give the title compound as an orange/brown oil.

IR (neat) 3239, 2970, 1741, 1684, 1607, 1408, 1375, 1233, 1040, 998, 844, 823 cm$^{-1}$;

$^1$H NMR (CDCl$_3$) δ7.93 (d, 2H, J=9.0Hz), 7.46 (d, 2H, J=9.0 Hz), 4.14 (s, 2H), 3.68 (t, 2H, J=7.5 Hz), 3.16 (t, 2H, J=7.5 Hz), 2.2 (m, 2H), 2.00 (s, 3H), 1.38 (s, 6H);

$^{13}$C NMR (CDCl$_3$) δ198.5, 170.9, 151.9, 134.8, 127.9, 126.2, 72.4, 44.6, 38.6, 35.2, 26.7, 25.7, 20.8;

MS (CI, CH$_4$) m/z (rel. intensity) 297 (MH$^+$, 56), 261 (59), 237 (100), 219 (52).

Step c: 4-[4-[4-(Hydroxydiphenylmethyl)-1-piperidinyl]-1-oxobutyl]-2,2-dimethylphenethyl alcohol Mix 4-(4-chloro-1-oxobutyl)-2,2-dimethylphenethyl acetate (99.5 g, 0.335 mol), α,α-diphenyl-4-piperidinemethanol (101.8 g, 0.335 mol), potassium hydrogen carbonate (83.8 g, 0.838 mol), potassium iodide (1.00 g, 0.006 mol), toluene (600 mL) and water (220 mL). Stir at reflux for 72 hours, add toluene (200 mL) and deionized water (100 mL). Filter through filter aid while at 80° C. and separate the organic phase. Dry (MgSO$_4$), filter and purify by chromatography (ethyl acetate) to give 4-[4-[4-(hydroxydiphenylmethyl)-1-piperidinyl]-1-oxobutyl]-2,2-dimethylphenethyl acetate as an oily solid.

IR (KBr) 3690, 3608, 3012, 2950, 2810, 1734, 1681, 1607, 1470, 1448, 1376, 1253, 1040, 997, 704, 667 cm$^{-1}$;

$^1$H NMR (CDCl$_3$) δ7.90 (d, 2H, J=8.2 Hz), 7.4 (m, 5H), 7.3 (m, 5H), 7.2 (m, 2H), 4.14 (s, 2H), 3.0 (m, 4H), 2.4 (m, 3H), 2.0 (m, 3H), 1.95 (s, 3H), 1.4 (m, 4H), 1.38 (s, 6H);

$^{13}$C NMR (CDCl$_3$) δ199.4, 170.9, 151.7, 145.8, 135.1, 128.1, 128.0, 126.5, 126.2, 125.7, 79.3, 72.5, 57.6, 53.7, 43.8, 38.6, 36.1, 25.7, 21.2, 20.8;

MS (CI, CH$_4$) m/z (rel. intensity) 528 (MH$^+$, 100), 510 (63), 450 (12), 293 (14).

Dissolve 4-[4-[4-(hydroxydiphenylmethyl)-1-piperidinyl]-1-oxobutyl]-2,2-dimethylphenethyl acetate (69.0 g, 0.131 mol) in methanol (2.5 L) and add 10% aqueous sodium hydroxide (769 mL, 1.92 mol). Stir at reflux for 1.5 hours, cool to 68° C. and evaporate the solvent in vacuo to a residue (700 mL). Add chloroform (1 L) and stir until solids are dissolved. Separate the organic phase and extract the aqueous phase with chloroform (3×300 mL). Combine the organic phases, dry (MgSO$_4$) and evaporate the solvent in vacuo and recrystallize (toluene) to give the title compound as a cream-colored powder; mp 135°–137° C.

IR (KBr) 3609, 3011, 2950, 2809, 2772, 1680, 1606, 1492, 1470, 1448, 1366, 1282, 1238, 1044, 791, 704, 668 cm$^{-1}$;

$^1$H NMR (CDCl$_3$) δ7.93 (d, 2H, J=8.2 Hz), 7.4 (m, 5H), 7.3 (m, 5H), 7.2 (m, 2H), 3.64 (s, 2H), 2.9 (m, 4H), 2.4 (m, 3H), 1.9 (M, 5H), 1.38 (s, 6H), 1.3 (m, 4H);

$^{13}$C NMR (CDCl$_3$) δ199.6, 152.1, 145.9, 135.2, 128.2, 126.4, 125.7, 79.5, 72.7, 57.8, 53.9, 44.0, 40.4, 36.2, 26.1, 25.2, 22.2;

MS (CI, CH$_4$) m/z (rel. intensity) 486 (MH$^+$, 100), 468 (81), 408 (19), 293 (23).

Step d: 4-[4-[4-(Hydroxydiphenylmethyl)-1-piperidinyl]-1-oxobutyl]-α,α-dimethylbenzeneacetic acid hydrochloride

METHOD A

Dissolve oxalyl chloride (1.57 g, 12.4 mmol) in methylene chloride (17 mL), cool to −55° C. and place under a nitrogen atmosphere. Add, by dropwise addition, a solution of dimethylsulfoxide (1.77 g, 1.61 mL) in methylene chloride (4.5 mL). Stir for 15 minutes and add, by dropwise addition, a solution of 4-[4-[4-(hydroxydiphenylmethyl)-1-piperidinyl]-1-oxobutyl]-2,2-dimethylphenethyl alcohol (5.0 g, 10.3 mol) in methylene chloride (33 mL). Stir for 30 minutes and add, by dropwise addition, triethylamine (7.2 mL). Stir for 15 minutes and then allow to warm to −10° C. Add a solution of oxone (12.66 g) in deionized water (50 mL). Stir for 15 minutes and add methylene chloride (25 mL). Separate the organic phase, wash with brine, dry (MgSO$_4$) and evaporate the solvent in vacuo. Purify by chromatography (ethyl acetate) to give 4-[4-[4-(hydoxydiphenylmethyl)-1-piperidinyl]-1-oxobutyl]-α,α-dimethylbenzeneacetaldehyde.

$^1$H NMR (CDCl$_3$) δ9.52 (s, 1H), 7.95 (d, 2H, J=8.2 Hz), 7.5 (m, 4H), 7.36 (d, 2H, J=8.2 Hz), 7.3 (m, 4H), 7.2 (m, 2H), 2.9 (m, 4H), 2.4 (m, 4H), 2.0 (m, 4H), 1.50 (s, 6H), 1.4 (m, 4H);

$^{13}$C NMR (CDCl$_3$) δ202, 199.9, 146.2, 136.2, 128.7, 128.3, 127.1, 126.6, 125.9, 79.4, 57.7, 53.8, 50.6, 43.9, 42.5, 36.2, 25.9, 22.3, 21.5;

MS (CI, CH$_4$) m/z (rel. intensity) 484 (MH$^+$, 76), 466 (100), 454 (19), 406 (16), 293 (16), 233 (19), 183 (49, 155 (54).

Dissolve 4-[4-[4-(hydroxydiphenylmethyl)-1-piperidinyl]-1-oxobutyl]-α,α-dimethylbenzeneacetaldehyde (3.40 g, 7.03 mmol) in acetone (30 mL) and cool to 15° C.

Add, by dropwise addition, 1N hydrochloric acid (10.5 mL). After addition of the hydrochloric acid is complete, add, by dropwise addition, a solution of potassium permanganate (1.82 g, 11.51 mmol) in acetone (80 mL). Stir at room temperature for 6 hours, filter and wash the filter cake with acetone (60 mL). Evaporate the filtrate in vacuo, dilute with methylene chloride (500 mL), dry (MgSO$_4$) and filter. Evaporate the solvent in vacuo and purify by chromatography (ethyl acetate) to give the title compound as a pale yellow solid.

IR (KBr) 3420, 3057, 2964, 1677, 1604, 1569, 1470, 1448, 1406, 1363, 1249, 1189, 1099, 750, 705 cm$^{-1}$;

$^1$H NMR (CDCl$_3$) δ7.75 (d, 2H, J=8.2 Hz), 7.4 (m, 6H), 7.2 (m, 4H), 7.1 (m, 2H), 3.9 (br. s, 2H), 3.1 (m, 2H), 2.9 (m, 2H), 2.6 (m, 2H), 2.3 (m, 2H), 1.9 (m, 3H), 1.7 (m, 2H). 1.44 (s, 6H), 1.4 (m, 2H);

$^{13}$C NMR (CDCl$_3$) δ199.4, 147.2, 134.5, 127.7, 127.5, 126.2, 125.7, 78.4, 57.3, 53.5, 46.6, 43.5, 35.6, 26.8, 25.9, 21.3;

MS (CI, CH$_4$) m/z (rel. intensity) 500 (MH$^+$, 79), 482 (62), 456 (100), 422 (30), 366 (42).

METHOD B

Mix 4-[4-[4-(hydoxydiphenylmethyl)-1-piperidinyl]-1-oxobutyl]-2,2-dimethylphenethyl alcohol (9.7 mmol), chloroform (20 mL), acetonitrile (20 mL), water (30 mL) and H$_5$IO$_6$ (5.6 g, 24.3 mmol). Add RuCl$_3$.5H$_2$O (0.15 g, 0.49 mmol) and stir at room temperature for 2 hours. Dilute the reaction mixture with methylene chloride (200 mL), wash with saturated NaHSO$_3$ (2×100 ML) and dry (MgSO$_4$). Filter, evaporate the filtrate in vacuo (20° C./60 torr) and purify by silica gel chromatography to give the title compound.

METHOD C

Mix K$_2$S$_2$O$_8$ (2.8 g, 10.2 mmol), KOH (85%, 1.95 g, 30 mmol) and water (20 mL). Add RuCl$_3$.5H$_2$O (30 mg, 0.2 mmol) and stir at room temperature for 5 minutes. Dissolve 4-[4-[4-(hydroxydiphenylmethyl)-1-piperidinyl]-1-oxobutyl]-2,2-dimethylphenethyl alcohol (0.97 mmol) in acetone (14 mL) and acetonitrile (2 mL) and add to the above solution. Stir at room temperature for 2.5 hours, filter and neutralize the filtrate with 1N HCl to pH 5. Extract with methylene chloride (2×50 mL), dry (MgSO$_4$), evaporate the solvent in vacuo (20° C./60 torr) and purify by silica gel chromatography to give the title compound.

METHOD D

Mix potassium permanganate (1.58 g, 10 mmol), water (4 mL) and acetic acid (26 mL). Cool to 5° C. and add phosporic acid (2.3 g of an 85% solution, 20 mmol). Stir vigorously and add, by dropwise addition, a solution of 4-[4-[4 -(hydroxydiphenylmethyl)-1-piperidinyl]-1-oxobutyl]-2,2-dimethylphenethyl alcohol (970 mg, 2.0 mmol) in acetic acid (5 mL) over 5 minutes. Stir at 5° C. for 2 hours, dilute with water (15 mL) and add Na$_2$S$_2$O$_5$ in small portions until the solution becomes colorless. Remove most of the acetic acid and water under vacuum and partition the residue between water (15 mL) and methylene chloride (60 ml). Separate the organic layer, wash sequentially with water (2×30 mL) and dilute hydrochloric acid (10%, 20 mL). Evaporate the solvent in vacuo to give the title compound as a light yellow foam (749 g, 70%).

MS (m/z) 500 (M+1); δ$^1$H NMR (DMSO-d$_6$) 7.79 (6H, m), 7.27 (4H, m), 7.14 (4H, t), 3.02 (4H, m), 2.51 (2H, m), 2.22 (2H, t), 1.81 (2H, m), 1.60 (3H, m), 1.44 (6H, s), 1.35 (2H, m).

Step e: 4-[4-[4-(Hydroxydiphenylmethyl)-1-piperidinyl]-1-hydroxybutyl]-α,α-dimethylbenzeneacetic acid hydrochloride

METHOD A

Add sodium borohydride (0.105 g, 2.77 mmol) to a solution of sodium hydroxide (0.053 g, 1.33 mmol) in deionized water (2 mL) and add, by dropwise addition, to a solution of 4-[4-[4-(hydroxydiphenylmethyl)-1-piperidinyl]-1-oxobutyl]-α,α-dimethylbenzeneacetic acid hydrochloride (0.70 g, 1.31 mmol) in ethanol (30 mL). Stir at room temperature for 3.5 hours at pH 7–8. Evaporate the solvent in vacuo and stir the residue with methylene chloride (15 mL) and deionized water (15 mL). Dry (MgSO$_4$), acidify to pH 3 with gaseous hydrogen chloride and evaporate the solvent. Add ether with stirring, filter the white solid and wash with additional ether. Dry to give the title compound.

IR (KBr) 3403, 3058, 2971, 1718, 1634, 1492, 1471, 1448, 1393, 1227, 1150, 1099, 1069, 839, 750, 706 cm$^{-1}$;

$^1$H NMR (CDCl$_3$) δ7.50 (d, 4H, J=8.2 Hz), 7.3 (m, 8H), 7.2 (m, 2H), 4.66 (t, 1H, J=5.6 Hz), 3.5 (m, 2H), 3.0 (m, 4H), 2.8 (m, 2H), 1.7 (m, 8H), 1.53 (s, 6H);

$^{13}$C NMR (CDCl$_3$) δ181.1, 147.4, 146.1, 144.4, 129.5, 128.0, 127.4, 127.2, 79.9, 73.9, 57.0, 54.1, 42.7, 36.8, 27.1, 25.7, 21.7;

MS (CI, CH$_4$) m/z (rel. intensity) 502 (MH$^+$, 50), 485 (33), 484 (100), 458 (25), 454 (33), 424 (17).

Anal. Calcd for C$_{32}$H$_{39}$NO$_4$·HCl·2.25H$_2$O (7.0% Tg): C, 66.42; H, 7.75; N, 2.42;

Found: C, 65.68; H, 7.48; N, 2.32 (6.8% Tg).

METHOD B

Dissolve 4-[4-[4-(hydroxydiphenylmethyl)-1-piperidinyl]-1-oxobutyl]-α,α-dimethylbenzeneacetic acid hydrochloride (2.0 g, 3.7 mmol) in ethanol (90 mL). Stir at room temperature for 10 minutes and add, by dropwise addition over 15 minutes, sodium borohydride (0.3 g, 8 mmol) and a solution of sodium hydroxide (0.16 g, 4 mmol) in water (5 mL). Stir for 30 minutes and cool in an ice-bath. Slowly add a solution made of concentrated hydrochloric acid (0.3 mL) and water (1 mL) to quench excess borohydride. Stir for 20 minutes and evaporate the solvent in vacuo. Partition the residue between chloroform (50 mL) and water (35 mL), separate the organic phase and extract the aqueous pase with chloroform (25 mL). Combine the organic phases and wash sequentially with water (20 mL) and 15% hydrochloric acid (15 mL). Evaporate the solvent in vacuo and dissolve the residue in methylene chloride (10 mL). Precipitate the product by dropwise addition of hexane and collect by filtration. Wash with hexane and air dry to give the title compound as a light yellow powder (0.96 g, 48%).

EXAMPLE 2

(R)-4-[4-[4-(Hydroxydiphenylmethyl)-1-piperidinyl]-1-hydroxybutyl]-α,α-dimethylbenzeneacetic, ethyl ester Dissolve (+)-B-chlorodiisopinocamphenylborane (2.5 g, 7.8 mmol) in anhydrous tetrahydrofuran (5 mL). Add a solution of 4-[4-[4-(hydroxydiphenylmethyl)-1-piperidinyl]-1-oxobutyl]-α,α-dimethylbenzeneacetic, ethyl ester (2 g, 3.54 mmol) in anhydrous tetrahydrofuran (5 mL). Stir at room temperature for 3 days and cool to 0° C. Add water (1 mL) and 30% hydrogen peroxide (2 mL) and stir for 20 minutes. Add methylene chloride (30 mL) and wash with brine (30 mL), then aqueous sodium hydrogen carbonate (30 mL), then brine (30 mL). Dry (MgSO$_4$), evaporate the solvent in vacuo and purify by chromatography (1:19 methanol:ethyl acetate) to give the title compound as a solid; mp 87°–90° C.

IR (KBr) 3436, 3058, 2932, 2813, 1725, 1632, 1599, 1470, 1448, 1255, 1147, 1097, 830, 749, 704 cm$^{-1}$;

$^1$H NMR (CDCl$_3$) δ7.5 (m, 4H), 7.3 (m, 8H), 7.2 (m, 2H), 4.6 (m, 1H), 4.08 (q, 2H, J=7.5 Hz), 3.1 (m, 1H), 3.0 (m, 1H), 2.4 (m, 3H), 2.0 (m, 3H), 1.7 (m, 5H), 1.53 (s, 6H), 1.5 (m, 2H), 1.42 (s, 2H), 1.15 (t, 3H, J=7.5 Hz);

[α]$_{20D}$ +39.4° (C=0.99, CHCl$_3$).

EXAMPLE 3

(S)-4-[4-[4-(Hydroxydiphenylmethyl)-1-piperidinyl]-1-hydroxybutyl]-α,α-dimethylbenzeneacetic acid, ethyl ester Dissolve (−)-B-chlorodiisopinocamphenylborane (2.5 g, 7.8 mmol) in anhydrous tetrahydrofuran (5 mL). Add a solution of 4-[4-[4-(hydroxydiphenylmethyl)-1-piperidinyl]-1-oxobutyl]-α,α-dimethylbenzeneacetic acid, ethyl ester (2 g, 3.54 mmol) in anhydrous tetrahydrofuran (5 mL). Stir at room temperature for 3 days and cool to 0° C. Add water (1 mL) and 30% hydrogen peroxide (2 mL) and stir for 20 minutes. Add methylene chloride (30 mL) and wash with brine (30 mL), then aqueous sodium hydrogen carbonate (30 mL), then brine (30 mL). Dry (MgSO$_4$), evaporate the solvent in vacuo and purify by chromatography to give the title compound.

What is claimed is:

1. A process for preparing a compound of the formula

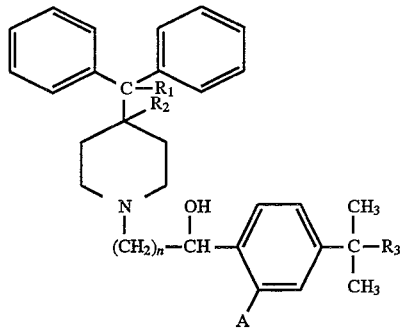

wherein

R$_1$ represents hydrogen or hydroxy;

R$_2$ represents hydrogen; or

R$_1$ and R$_2$ taken together form a second bond between the carbon atoms bearing R$_1$ and R$_2$;

n is an integer of from 1 to 5;

R$_3$ is —CH$_2$OH;

A is hydrogen or hydroxy; and pharmaceutically acceptable salts, hydrates and individual optical isomers thereof comprising the steps of:

(a) reacting a benzeneacetic acid compound of the formula

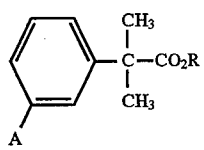

wherein A is as defined above and R is hydrogen or $C_1$–$C_6$ alkyl with a suitable reducing agent to give a phenethyl alcohol;

(b) reacting the phenethyl alcohol with a ω-halo compound of the formula

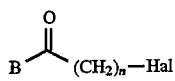

wherein wherein B is halo or hydroxy, Hal represents Cl, Br or I and n is as defined above, in the presence of a suitable Lewis acid to produce a ω-halo hydroxyethylphenylketone;

(c) reacting the ω-halo hydroxyethylphenylketone with a piperidine compound of the formula

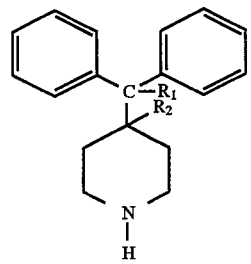

wherein $R_1$ and $R_2$ are as defined above, in the presence of a suitable non-nucleophilic base to produce a piperidine hydroxyethylphenylketone;

(d) reacting the piperidine hydroxyethylphenylketone with a suitable reducing agent to produce a piperidine hydroxyethylphenylalcohol; and (e) optionally reacting the piperidine hydroxyethylphenylalcohol with an appropriate deprotecting reagent, with the proviso that each of the hydroxy groups present in the compounds described in steps a–d are optionally protected or unprotected.

2. A process according to claim 1 wherein the reducing agent of step d is (+)-B-chlorodiisopinocamphenylborane.

3. A process according to claim 1 wherein the reducing agent of step d is (−)-B-chlorodiisopinocamphenylborane.

* * * * *

UNITED STATES PATENT AND TRADEMARK OFFICE
CERTIFICATE OF CORRECTION

PATENT NO. : 5,654,433

DATED : August 5, 1997

INVENTOR(s) : Chi-Hsin Richard King; Michele A. Kaminski

It is certified that error appears in the above-identified patent and that said Letters Patent is hereby corrected as shown below:

Column 6, Line 1 of Patent reads "latice" and should read --lattice--.

Column 7, Line 64 of Patent reads "art of are prepared" and should read --art or are prepared--.

Column 9, Line 11 of Patent reads "a appropriate" and should read --an appropriate--.

Column 10, Line 51 of Patent reads "alkyation" and should read --alkylation--.

Column 16, Line 24 of Patent reads "(MgSO4)" and should read --($MgSO_4$)--.

Column 18, Line 24 of Patent reads "(hydoxydiphenylmethyl)" and should read --(hydroxydiphenylmethyl)--.

Column 19, Line 47 of Patent reads "pase" and should read --phase--.

Column 20, Line 15 of Patent reads "$[\alpha]_{20D}$" and should read --$[\alpha]^{20}_D$--.

Column 21, Line 21 of Patent reads "wherein, wherein" and should read --wherein--.

Signed and Sealed this

Twenty-fifth Day of August, 1998

Attest:

BRUCE LEHMAN

*Attesting Officer*    *Commissioner of Patents and Trademarks*